US012367258B2

(12) United States Patent
Takagi et al.

(10) Patent No.: US 12,367,258 B2
(45) Date of Patent: Jul. 22, 2025

(54) IMPORTANCE ANALYSIS APPARATUS, METHOD, AND NON-TRANSITORY COMPUTER READABLE MEDIUM (71) Applicant: KABUSHIKI KAISHA TOSHIBA, Tokyo (JP)

(72) Inventors: Kentaro Takagi, Yokohama (JP); Kouta Nakata, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 1012 days.

(21) Appl. No.: 17/187,374

(22) Filed: Feb. 26, 2021

(65) Prior Publication Data

US 2022/0076049 A1 Mar. 10, 2022

(30) Foreign Application Priority Data

Sep. 10, 2020 (JP) .................. 2020-151951

(51) Int. Cl.
G06N 20/00 (2019.01)
G06F 18/21 (2023.01)
G06F 18/2113 (2023.01)

(52) U.S. Cl.
CPC ...... *G06F 18/2113* (2023.01); *G06F 18/2163* (2023.01); *G06N 20/00* (2019.01)

(58) Field of Classification Search
None
See application file for complete search history.

(56) References Cited

U.S. PATENT DOCUMENTS

2018/0260646 A1* 9/2018 Hara .................. G06F 18/2321
2021/0090694 A1* 3/2021 Colley ................ G16H 15/00

FOREIGN PATENT DOCUMENTS

CN 110442941 A * 11/2019

OTHER PUBLICATIONS

Fan (Year: 2019).*
Project Cabinet Blog, Evolutionary? Boxplot, [online], http://k-metrics.netlify.app/post/2018-09/violinplot, Sep. 26, 2018, (with English Translation), 12 pages.
Andre Altmann, et al. "Permutation importance: a corrected feature importance measure" Bioinformatics, vol. 26, Issue 10, May 15, 2010, pp. 1340-1347.
Karen Simonyan, et al., "Deep Inside Convolutional Networks: Visualising Image Classification Models and Saliency Maps", arXiv: 1312.6034v2 [cs.CV], Apr. 19, 2014, 8 pages.

* cited by examiner

*Primary Examiner* — David R Vincent
(74) *Attorney, Agent, or Firm* — Oblon, McClelland, Maier & Neustadt, L.L.P.

(57) ABSTRACT

According to one embodiment, the importance analysis apparatus includes an importance calculator and a distribution calculator. Based on a trained model and a plurality of input data samples, the importance calculator calculates an importance of each of a plurality of feature amounts of each of the input data samples. The distribution calculator calculates a distribution of the importances of each of the feature amounts across the input data samples.

13 Claims, 6 Drawing Sheets

F I G. 1

F I G. 2

$x^1, x^2, x^3, x^4 \rightarrow$ Feature amount

Input data sample #1 $(x_1^1, x_1^2, x_1^3, x_1^4) = (0.1, 0.4, 0.1, 0.8)$

Input data sample #2 $(x_2^1, x_2^2, x_2^3, x_2^4) = (0.8, 0.5, 0.9, 0.7)$

Input data sample #3 $(x_3^1, x_3^2, x_3^3, x_3^4) = (0.7, 0.1, 0.7, 0.8)$ $\vdots$ Input data sample #N $(x_N^1, x_N^2, x_N^3, x_N^4) = (0.2, 0.1, 0.1, 0.8)$

FIG. 3

$x^1, x^2, x^3, x^4 \rightarrow$ Feature amount
$y \rightarrow$ Estimated output value Input data sample #1 $(x_1^1, x_1^2, x_1^3, x_1^4, y_1) = (0.1, 0.4, 0.1, 0.8, 0.9)$ Input data sample #2 $(x_2^1, x_2^2, x_2^3, x_2^4, y_2) = (0.8, 0.5, 0.9, 0.7, 0.1)$ Input data sample #3 $(x_3^1, x_3^2, x_3^3, x_3^4, y_3) = (0.7, 0.1, 0.7, 0.8, 0.4)$ $\vdots$ Input data sample #N $(x_N^1, x_N^2, x_N^3, x_N^4, y_N) = (0.2, 0.1, 0.1, 0.8, 0.9)$

FIG. 4

$c^1, c^2, c^3, c^4 \rightarrow$ Importance

Input data sample #1 $(c_1^1, c_1^2, c_1^3, c_1^4) = (0.1, 0.4, 0.1, 0.8)$

Input data sample #2 $(c_2^1, c_2^2, c_2^3, c_2^4) = (0.2, 0.5, 0.2, 0.7)$

Input data sample #3 $(c_3^1, c_3^2, c_3^3, c_3^4) = (0.7, 0.1, 0.8, 0.2)$ $\vdots$ Input data sample #N $(c_N^1, c_N^2, c_N^3, c_N^4) = (0.4, 0.1, 0.1, 0.8)$

IMPORTANCE ANALYSIS APPARATUS, METHOD, AND NON-TRANSITORY COMPUTER READABLE MEDIUM

CROSS-REFERENCE TO RELATED APPLICATIONS

This application is based upon and claims the benefit of priority from Japanese Patent Application No. 2020-151951, filed Sep. 10, 2020, the entire contents of which are incorporated herein by reference.

FIELD

Embodiments described herein relate generally to an importance analysis apparatus, method, and non-transitory computer readable medium.

BACKGROUND

When machine learning is actually used, there may arise a demand for calculating, from a trained model, an importance of a feature amount relating to input data. For example, it is conceivable to refer to importances in order to omit unnecessary dimensions when input data has many feature amounts and has many dimensions. It is also conceivable to construct a yield or performance prediction model, and extract a feature amount having great influence on the yield or performance.

There is a method of calculating, as an importance in machine learning, an average importance of a feature amount of all input data samples. Since an average importance across all input data samples is calculated, there is a possibility of overlooking the case where feature amounts of high importances are only in some input data samples out of all input data samples, the case where a distribution of importances is multimodal, or the like. There is a method of calculating an importance of a feature amount of each input data sample; however, the method cannot calculate importances across all input data samples.

DETAILED DESCRIPTION

In general, according to one embodiment, an importance analysis apparatus includes an importance calculator and a distribution calculator. Based on a trained model and a plurality of input data samples, the importance calculator calculates an importance of each of a plurality of feature amounts of each of the input data samples. The distribution calculator calculates a distribution of the importances of each of the feature amounts across the input data samples.

Hereinafter, an importance analysis apparatus, method, and non-transitory computer readable medium according to the present embodiment will be described with reference to the accompanying drawings.

Figure 1:
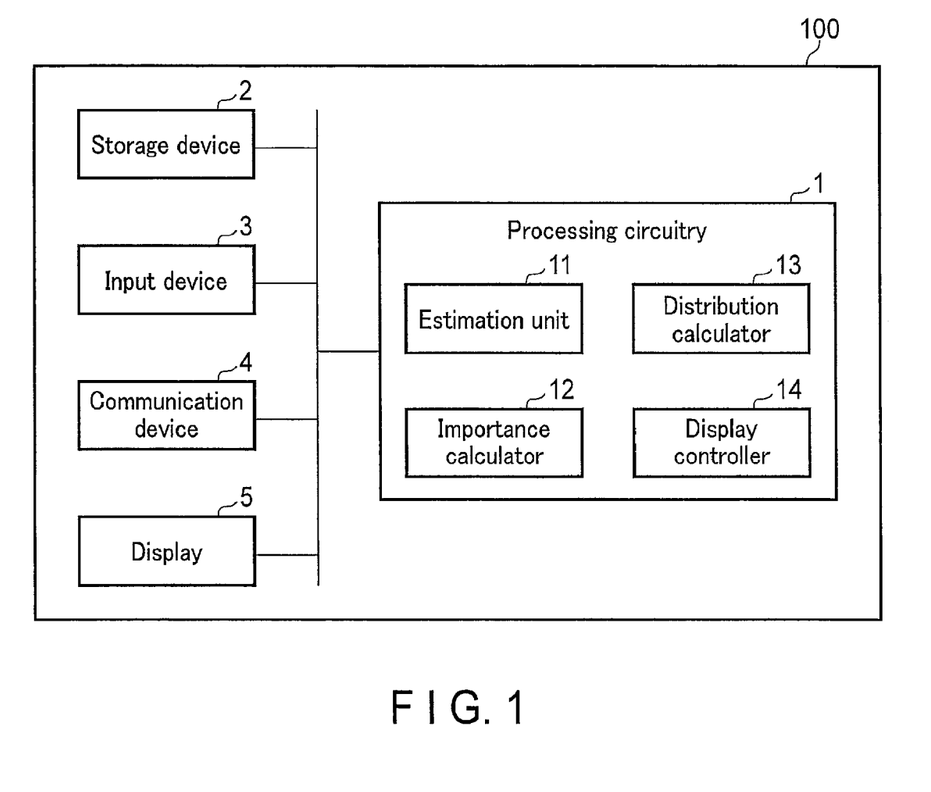
FIG. 1 shows a configuration example of an importance analysis apparatus according to the present embodiment.

FIG. 1 shows a configuration example of an importance analysis apparatus 100 according to the present embodiment. The importance analysis apparatus 100 is a computer for analyzing an importance of a feature amount in machine learning. As shown in FIG. 1, the importance analysis apparatus 100 includes processing circuitry 1, a storage device 2, an input device 3, a communication device 4, and a display 5.

The processing circuitry 1 includes a processor such as a central processing unit (CPU), and a memory such as a random access memory (RAM). The processing circuitry 1 executes importance visualization processing for calculating and visualizing an importance of a feature amount in machine learning. The processing circuitry 1 executes a program stored in the storage device 2 to implement an estimation unit 11, an importance calculator 12, a distribution calculator 13, and a display controller 14. Hardware implementation of the processing circuitry 1 is not limited to this. For example, the processing circuitry 1 may be constituted by a circuit, such as an application specific integrated circuit (ASIC), which implements the estimation unit 11, the importance calculator 12, the distribution calculator 13, and/or the display controller 14. The estimation unit 11, the importance calculator 12, the distribution calculator 13, and/or the display controller 14 may be implemented in a single integrated circuit, or implemented respectively in a plurality of integrated circuits.

The estimation unit 11 calculates an output value (hereinafter referred to as an "estimated output value") by applying each of a plurality of input data samples to a trained model. The trained model according to the present embodiment is a neural network trained to output an estimated output value in response to input of an input data sample. The trained model according to the present embodiment is a neural network that performs classification and regression. The input data sample may be numerical data or image data. The output value is a numerical value, such as a score, probability, or ratio of each class. It is possible to output image data in a preceding stage of the output layer, and to output an estimated output value based on the image data from the output layer.

Based on a trained model and a plurality of input data samples, the importance calculator 12 calculates an importance of each of a plurality of feature amounts of each of the input data samples. The importance is an index for evaluating the degree of influence of each feature amount on the estimated output value.

The distribution calculator 13 calculates a distribution of importances of each of a plurality of feature amounts across the input data samples. The distribution is that relating to the frequency of occurrence, probability, probability density, or the like of each numerical value of importance. Typically, a probability density function is calculated as the distribution.

The display controller 14 causes the display 5 to display various types of information. For example, the display controller 14 visualizes the distribution. Specifically, the display controller 14 generates a graph showing a distribution for each of a plurality of feature amounts, and causes the display 5 to display the graph.

The storage device 2 is constituted by a read only memory (ROM), a hard disk drive (HDD), a solid state drive (SSD), and an integrated circuit storage device, or the like. The storage device 2 stores results of various operations by the processing circuitry 1, various programs executed by the processing circuitry 1, and the like. The storage device 2 also stores a trained model, a plurality of input data samples, and the like.

Through the input device 3, various commands from the user are input. As the input device 3, a keyboard, a mouse, various switches, a touch pad, a touch panel display, and the like can be used. An output signal from the input device 3 is supplied to the processing circuitry 1. The input device 3 may be a computer connected to the processing circuitry 1 by wire or radio.

The communication device 4 is an interface for performing information communication with an external device connected to the importance analysis apparatus 100 via a network.

The display 5 displays various types of information. For example, the display 5 displays a graph showing a distribution in accordance with control by the display controller 14. As the display 5, a cathode-ray tube (CRT) display, a liquid crystal display, an organic electroluminescence (EL) display, a light-emitting diode (LED) display, a plasma display, or any other display known in the relevant technical field may be used as appropriate.

Hereinafter, the importance analysis apparatus 100 according to the present embodiment will be described in detail.

Figure 2:
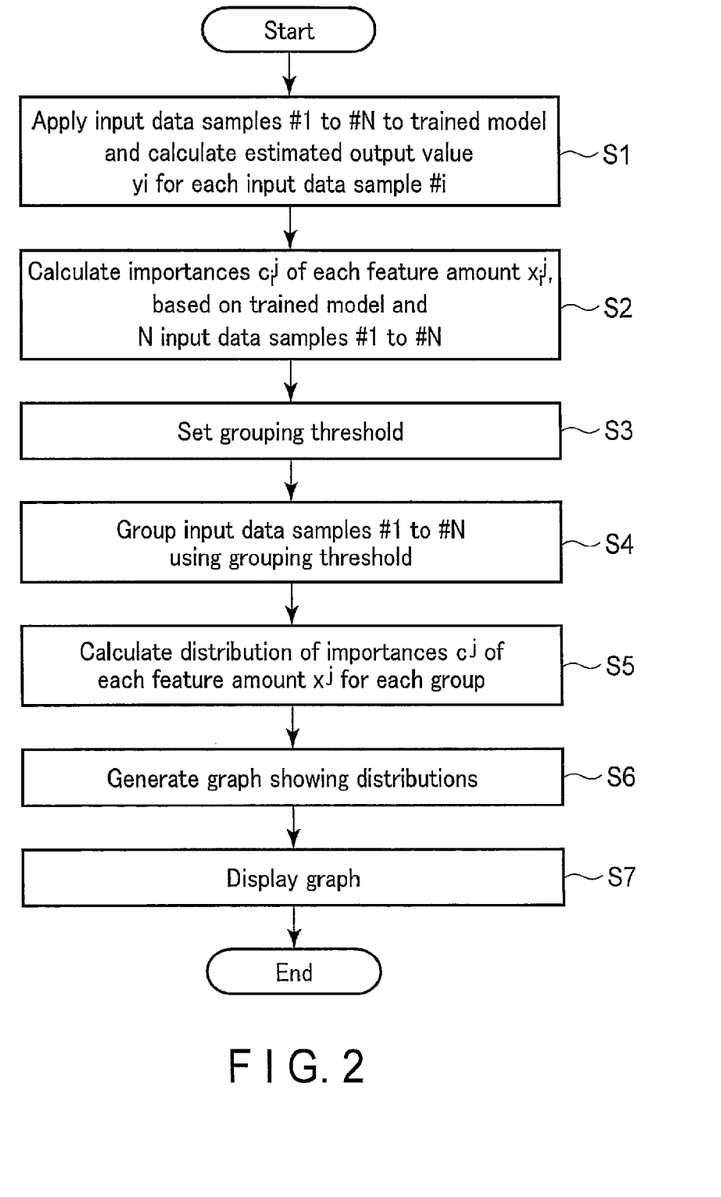
FIG. 2 shows an example of the flow of importance visualization processing by processing circuitry in FIG. 1.

FIG. 2 is a diagram showing an example of the flow of importance visualization processing by the processing circuitry 1. In response to input of a command to start importance visualization processing by the user via the input device 3, or the like, the processing circuitry 1 reads a program relating to the importance visualization processing from the storage device 2, and executes the program. Through execution of the program, the processing circuitry 1 implements the series of processes and functions shown in FIG. 2. The program may be constituted by a single module that implements the series of processes and functions shown in FIG. 2, or may be constituted by a plurality of modules that share the series of processes and functions.

As shown in FIG. 2, the estimation unit 11 applies N input data samples #i to a trained model and calculates an estimated output value yi for each input data sample #i (step S1). N is an integer greater than or equal to 2, which indicates the number of input data samples. i is an integer in the range of $1 \leq i \leq N$, which indicates the number of an input data sample. The input data may be numerical data, image data, or other data.

In step S1, the estimation unit 11 applies an input data sample #i to a trained model and performs forward propagation processing, thereby estimating an estimated output value yi, which is an objective variable of the trained model. The trained model according to the present embodiment is a neural network for multi-class classification and regression, and the estimated output value yi is a plurality of discrete values or continuous values. The estimation unit 11 calculates feature amounts $x_i^j$ of J dimensions (J feature amounts $x_i^j$) in the estimation process of the forward propagation processing. J is an integer greater than or equal to 2 which indicates the number of dimensions of feature amounts (number of feature amounts). j is an integer in the range of $1 \leq j \leq J$ which indicates the dimension number of a feature amount. The feature amount $x_i^j$ is the feature amount of the j-th dimension of the feature amounts of J dimensions included in the i-th input data sample #i. The feature amount $x_i^j$ is an index representing a feature amount of the input data #i. The feature amount $x_i^j$ corresponds to, for example, a feature map or a feature vector acquired by forward propagation of a convolution layer included in the trained model. The estimation unit 11 estimates the estimated output value yi from the input data sample #i through the feature amounts $x_i^j$ of J dimensions. The feature amount $x_i^j$ need not necessarily be estimated by forward propagation of the trained model. For example, when the input data sample #i is manufacturing data, the feature amount $x_i^j$ may be a numerical value representing manufacturing data, or a statistical operation value, such as an average value, a variance value, or a standard deviation, based on manufacturing data. When the input data sample #i is image data, the feature amount $x_i^j$ may be a pixel value such as a luminance, or a feature amount calculated by analysis of texture, such as an edge, granularity, or the like, based on a luminance distribution. These feature amounts $x_i^j$ may be calculated by an analytical method without using the trained model.

Figure 3:
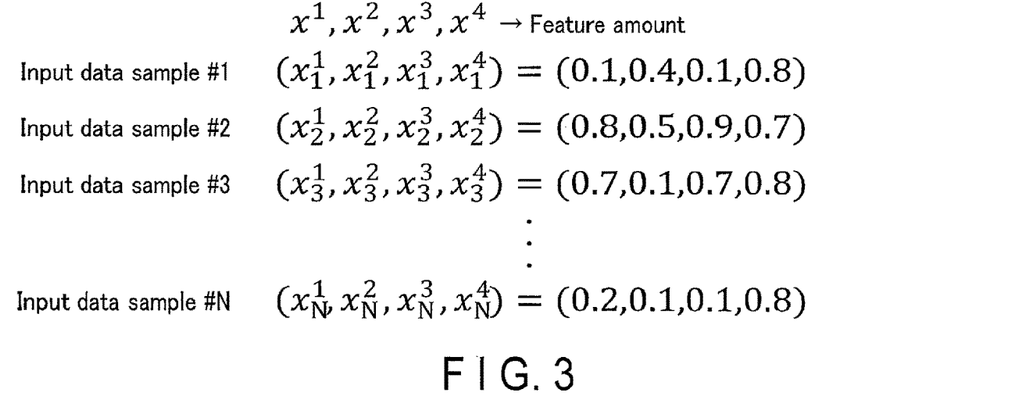
FIG. 3 shows an example of feature amounts $x_i^f$ of each input data sample #i.

FIG. 3 shows an example of feature amounts $x_i^j$ of each input data sample #i. In FIG. 3, the number J of dimensions of feature amounts is 4. For example, the input data sample #1 has a first-dimension feature amount $x_1^1$, a second-dimension feature amount $x_1^2$, a third-dimension feature amount $x_1^3$, and a fourth-dimension feature amount $x_1^4$, which are 0.1, 0.4, 0.1, and 0.8, respectively. The same applies to the other input data samples #i.

Figure 4:
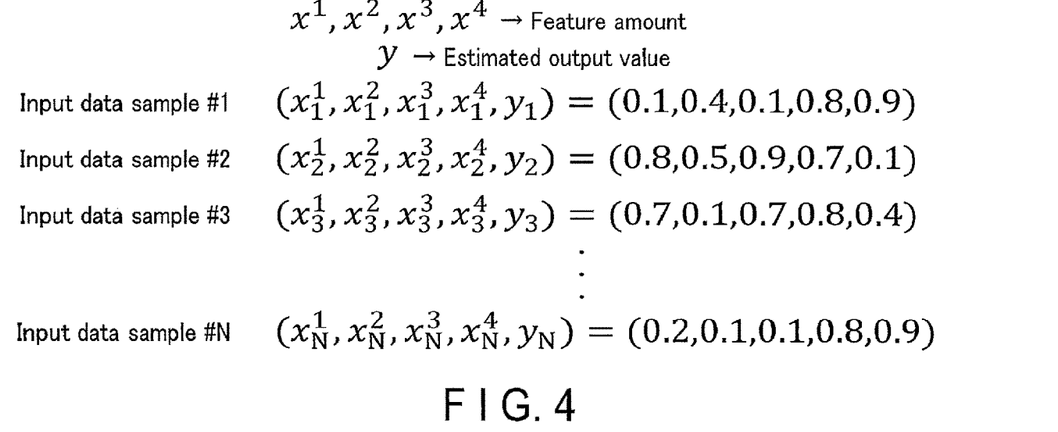
FIG. 4 shows an example of feature amounts $x_i^j$ and an estimated output value yi of each input data sample #i.

FIG. 4 shows an example of feature amounts $x_i^j$ and an estimated output value yi of each input data sample #i. The input data samples of FIG. 4 are the same as those in FIG. 3. For example, the estimated output value y1 for the input data sample #1 is 0.9. The same applies to the other estimated output values yi. Each estimated output value yi is stored in the storage device 2 in a manner associated with an input data sample #i.

Hereinafter, an example of each of the trained model, input data, and estimated output value will be described. An example of the trained model is a yield estimation model of semiconductor manufacturing chips. As input data for the yield estimation model, optical image data acquired by performing optical imaging on a plurality of semiconductor chips is used. By the optical image data being input to the yield estimation model, an estimated output value, which is a defectiveness and/or non-defectiveness determination result as to semiconductor chips rendered in the optical image data, is acquired. As the estimated output value, for example, the number of defective ones and/or non-defective ones of the semiconductor chips rendered in the optical image data, the defectiveness and/or non-defectiveness probability, a label indicating a type of defect of a defective semiconductor chip, or the like is acquired. The estimated output value can be acquired for each semiconductor chip rendered in optical image data or each pixel of the data.

Another example of the trained model is a disease morbidity estimation model. As input data for the morbidity estimation model, medical image data acquired by various medical image diagnosis apparatuses performing medical imaging on patients is used. By the medical image data being input to the morbidity estimation model, an estimated output value, which is a result of determination of whether the patient rendered in the medical image data is affected or unaffected, is acquired. As the estimated output value, for example, whether or not a human body site rendered in medical image data is affected by a specific disease, the probability of morbidity of a specific disease, or the like is acquired. The estimated output value can be acquired for each medical image data sample, or each region of interest or pixel of medical image data.

After step S1, the importance calculator 12 calculates an importance $c_i^j$ of each feature amount $x_i^j$ for each input data sample #i, based on the trained model and N input data samples #1 to #N (step S2). Specifically, in step S2, the importance calculator 12 calculates an importance $c_i^j$ of each feature amount $x_i^j$ by measuring a change in the estimated output value yi of the trained model with respect to a change in the feature amount $x_i^j$. The importance can be calculated by a method such as saliency mapping or occlusion sensitivity. For example, when saliency mapping is used, the importance calculator 12 calculates an importance $c_i^j$ for each feature amount $x_i^j$ by differentiating the estimated output value yi with respect to the feature amount $x_i^j$.

Figure 5:
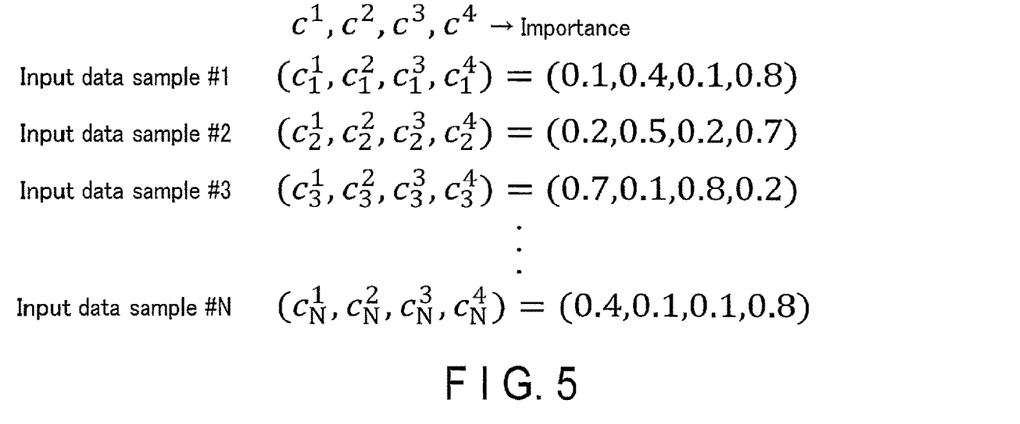
FIG. 5 shows an example of importances $c_i^j$ of each input data sample #i.

FIG. 5 shows an example of importances $c_i^j$ of each input data sample #i. The input data samples of FIG. 5 are the same as those in FIGS. 3 and 4. For example, regarding the input data sample #1, the importance $c_1^1$ corresponding to the first-dimension feature amount $x_1^1$, the importance $c_1^2$ corresponding to the second-dimension feature amount $x_1^2$, the importance $c_1^3$ corresponding to the third-dimension feature amount $x_1^3$, and the importance $c_1^4$ corresponding to the fourth-dimension feature amount $x_1^4$ are 0.4, 0.1, 0.4, and 0.8, respectively. The same applies to the other importances $c_i^j$. Each importance $c_i^j$ is stored in the storage device 2 in a manner associated with an input data sample #i and an estimated output value yi.

After step S2, the distribution calculator 13 sets a grouping threshold (step S3). The grouping threshold is a threshold for grouping input data samples #1 to #N in accordance with their estimated output values yi. The grouping threshold may be set at, for example, a value designated by the user at a user interface included in the display controller 14. The number of grouping thresholds may be one or more. The grouping threshold may be set at any value which the estimated output value yi may take. In the present embodiment, there is one grouping threshold, which is set at 0.5.

After step S3, the distribution calculator 13 groups N input data samples #1 to #N using the grouping threshold (step S4). In step S4, the distribution calculator 13 groups N input data samples #1 to #N by applying the grouping threshold to a plurality of estimated output values yi. When the number of grouping thresholds is one, for each input data sample #i, the distribution calculator 13 determines the magnitude relationship between the estimated output value yi and the grouping threshold, classifies the input data sample #i into group G1 when the estimated output value yi is smaller than the grouping threshold, and classifies the input data sample #i into group G2 when the estimated output value yi is greater than or equal to the grouping threshold. For example, in the case of FIG. 4, the estimated output value y2 of the input data sample #2 is 0.1 and the estimated output value y3 of the input data sample #3 is 0.4. Since these estimated output values are smaller than the grouping threshold, the input data samples #2 and #3 are classified into group G1. The estimated output value y2 of the input data sample #1 is 0.9, and the estimated output value yN of the input data sample #N is 0.9. Since these estimated output values are greater than or equal to the grouping threshold, the input data samples #1 and #N are classified into group G2.

After step S4, the distribution calculator 13 calculates a distribution of importances $c^j$ for each feature amount $x^j$ for each group (step S5). The feature amounts $x^j$ represent the j-th feature amounts of all input data samples #1 to #N. The type of distribution calculated in step S5 can be set in accordance with the form of display of distribution by the display controller 14. The type of distribution can be discretionarily selected from among a probability density function, an average, a standard deviation, a quantile, and the like. For example, when the type of distribution is the probability density function, the distribution calculator 13 calculates, regarding the j-th feature amount $x^j$, a probability density function of importances $c^j$, based on the importances $c^j$ of all input data samples #1 to #N belonging to group G1. Similarly, the distribution calculator 13 calculates, regarding the j-th feature amount $x^j$, a probability density function of importances $c^j$, based on the importances $c^j$ of all input data samples #1 to #N belonging to group G2. Similarly, for each of the J feature amounts $x^j$, a probability density function is calculated for each group. The probability density function may be calculated by an existing method.

After step S5, the display controller 14 generates a graph showing the distributions (step S6). After step S6, the display controller 14 causes the graph to be displayed (step S7). The display controller 14 generates a graph showing a distribution of each of the J feature amounts $x^j$ for each group, and causes the display 5 to display the generated graph. The graph includes a first graph defined by importances $c^j$ and J feature amounts $x^j$. The distribution of each of the J feature amounts $x^j$ is shown by a second graph defined by importances $c^j$ and distribution values indicating frequencies of occurrence of the importances $c^j$. The second graph is generated for each group. The second graphs of the J feature amounts $x^j$ are aligned in such a manner that the directions of their axes of importance $c^j$ match that of the first graph.

The display controller 14 generates a graph of a type corresponding to the type of the distribution calculated in step S5. For example, when the distribution is a probability density function, a violin plot may be generated as the graph.

Figure 6:
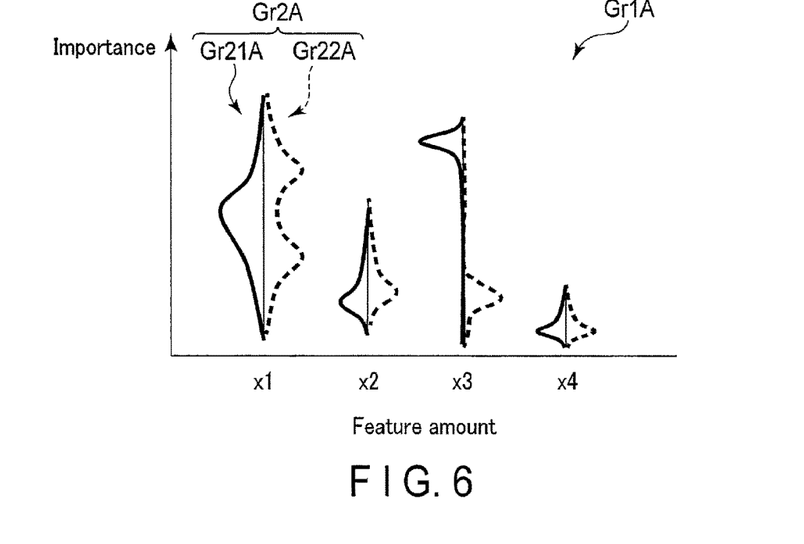
FIG. 6 shows a display example (with grouping) of a violin plot.

FIG. 6 shows a display example of the violin plot. The violin plot in FIG. 6 shows, as an example, the case where the number of grouping thresholds is one, and the distribution is a probability density function. As shown in FIG. 6, the violin plot includes a first graph Gr1A in which the vertical axis represents importances $c^j$ and the horizontal axis represents J feature amounts $x^j$. The violin plot also includes a second graph Gr2A for each feature amount $x^j$, in which the vertical axis represents importances $c^j$ and the horizontal axis represents probability densities of the importances $c^j$. The second graphs Gr2A each have the axis of importance $c^j$ pointing in the same direction as the axis of importance in the first graph Gr1A, and are aligned along the axis of feature amount $x^j$. The second graphs Gr2A each include a graph Gr21A of group G1 and a graph Gr22A of group G2. In the graph Gr21A, the vertical axis represents importances $c^j$, the horizontal axis represents probability densities, and the leftward direction on the figure is defined as the plus direction. In the graph Gr22A, the vertical axis represents importances $c^j$, the horizontal axis represents probability densities, and the rightward direction on the figure is defined as the plus direction. The graph Gr21A and graph Gr22A share the vertical axis.

The waveform of the probability density function of the graph Gr21A and that of the graph Gr22A are displayed differently in terms of visual appearance, such as color or type of line. For example, the waveform of the probability density function of the graph Gr21A may be shown in blue, and that of the graph Gr22A may be shown in orange. This makes it possible to observe the waveforms of the groups while visually distinguishing one from another easily.

The display example of FIG. 6 enables observation and analysis of the probability density function of importances of each feature amount across all of N input data samples for each group. Since importances are visualized for each of the groups formed according to estimated output values, it is possible to observe and analyze behaviors of importances corresponding to estimated output values. Since importances of each feature amount are visualized for each group, it is possible to observe and analyze behaviors of importances corresponding to feature amounts, differences in behavior corresponding to estimated output values, and the like. For example, it is possible to find out that the probability density functions of importances are different between group G1 and group G2, as in the graphs of the feature amount $x^1$ and the feature amount $x^3$.

Regarding the feature amount $x^1$, the input data samples in group G2 constitute a multimodal (bimodal) waveform, which has a probability density peak at two importances. The input data samples in group G1 constitute a unimodal waveform, which has a probability density peak at one importance. It can be understood that, regarding the feature amount $x^3$, the waveform of the input data samples in group G1 has a probability density peak at a high importance, and the waveform of the input data samples in group G2 has a probability density peak at a low importance. Namely, it can be understood that the importances vary with estimated output values, and the importances of the feature amounts $x^3$ are high regarding the input data samples belonging to group G1 in particular. If an average importance is visualized without grouping, one value (average importance) is visualized, and it is overlooked that the importances of the feature amount $x^3$ of the input data samples belonging to group G1 are high. The present display example can visualize that the importances of the feature amounts $x^3$ are high regarding the input data samples belonging to group G1, and thus can lower the probability of overlooking a significant feature amount. Detecting a feature amount of high importance enables, for example, generation of a low-cost trained model obtained by extracting only the operation parts relating to the feature amount, or analysis of the feature amount. In addition, in the case of the yield estimation model or the like, a feature amount of high importance regarding some input data samples with a low yield can be extracted; therefore, a manufacturing device or the like that seems to be a cause for a deteriorated yield can be quickly and easily identified by identifying a manufacturing device relating to the extracted feature amount.

The display controller 14 may place the distributions of the J feature amounts $x^j$ in descending order of difference in distribution between groups. For example, in the case of the example of FIG. 6, the display controller 14 may calculate a difference value between a probability density of group G1 and a probability density of group G2 for each feature amount $x^j$, and cause the graphs Gr2A to be displayed in descending order of difference value from left. This enables the user to more efficiently and more reliably observe and analyze a graph Gr2A in which the difference in probability density between groups is large. Alternatively, the display controller 14 may calculate a difference value between a probability density of group G1 and a probability density of group G2 corresponding to a specific importance, and cause the graphs Gr2A to be displayed in descending order of difference value from the left. The specific importance may be set to, for example, a peak value or the like of each probability density function.

The display controller 14 may enhance a distribution of the distributions of the J feature amounts $x^j$, in which the difference in distribution between groups is larger than a threshold. For example, in the case of the example of FIG. 6, the display controller 14 may calculate a difference value between a probability density of group G1 and a probability density of group G2 for each feature amount $x^j$, and enhance, with a visual effect such as color or flashing, a graph Gr2A in which the difference value is larger than a threshold. Alternatively, a mark or message indicating that the difference value is larger than a threshold may be attached to the graph Gr2A. This enables the user to more efficiently and more reliably observe and analyze a graph Gr2A in which the difference in probability density function between groups is large.

The importance visualization processing accordingly finishes.

The above importance visualization processing is an example, and can be modified in various ways.

Figure 7:
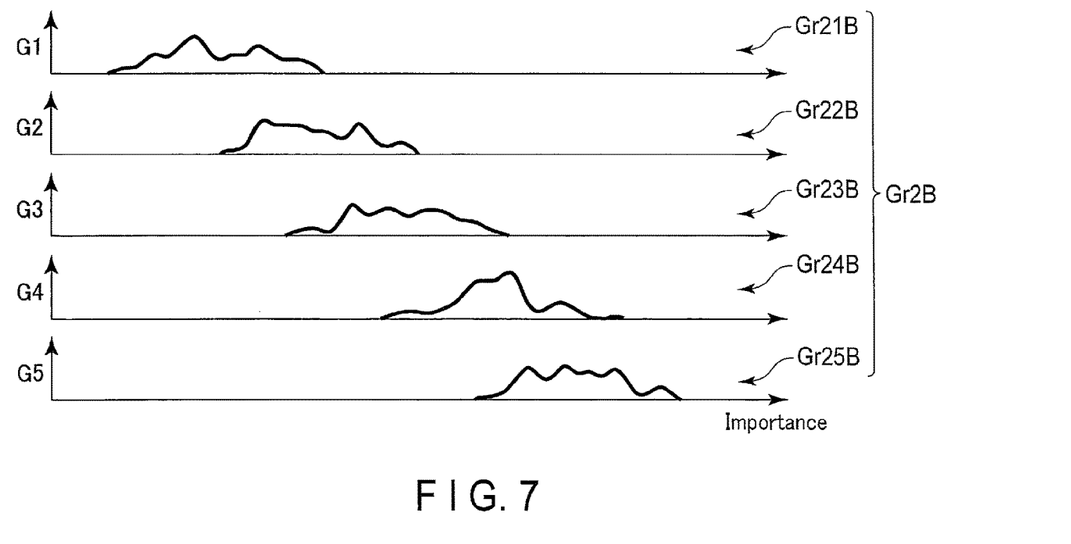
FIG. 7 shows a display example of a ridgeline plot.

For example, the number of grouping thresholds may be two or more. In this case, the distribution calculator 13 may divide N input data samples #1 to #N into three or more groups using the two or more grouping thresholds. In this case, the distribution calculator 13 may select any two groups from the three or more groups, and calculate distributions of importances in the above-described manner for the two selected groups. The two groups may be designated by the user via the input device 3 or automatically selected. The distribution calculator 13 may also calculate a distribution of importances for each of the three or more groups. In this case, the display controller 14 may generate a ridgeline plot as a graph showing distributions and cause the ridgeline plot to be displayed.

FIG. 7 shows a display example of the ridgeline plot. The ridgeline plot Gr2B shown in FIG. 7 is a set of five graphs Gr21B to Gr25B corresponding respectively to five groups G1 to G5 regarding a single feature amount. Each graph shows a probability density function with the vertical axis representing probability densities and the horizontal axis representing importances. The display controller 14 causes the five graphs Gr21B to Gr25B regarding a single feature amount to be displayed in an aligned manner. This enables the user to comprehensively view the probability density functions of importances across the five groups G1 to G5.

The graph of the case of three or more groups is not limited to a ridgeline plot. For example, the graph may be a 3D violin plot. In this case, the display controller 14 may generate graphs of probability density functions of a plurality of importances corresponding to a plurality of groups and arrange the graphs in a three-dimensional space while sharing the importance axis, thereby generating a 3D violin plot and causing the 3D violin plot to be displayed. The 3D violin plot may be displayed in such a manner that the view can be changed in accordance with a command input by the user through the input device 3. In addition, the display controller 14 may adopt any display method which enables visual recognition of a plurality of graphs. For example, a plurality of graphs may be displayed in an overlapping manner, in a stacked manner, or another manner, with different visual effects, such as colors.

In the above embodiment, the trained model outputs an estimated output value of one channel. However, the present embodiment is not limited to this. The trained model may output estimated output values of a plurality of channels. In this case, steps S2 to S7 may be performed for each channel.

Figure 8:
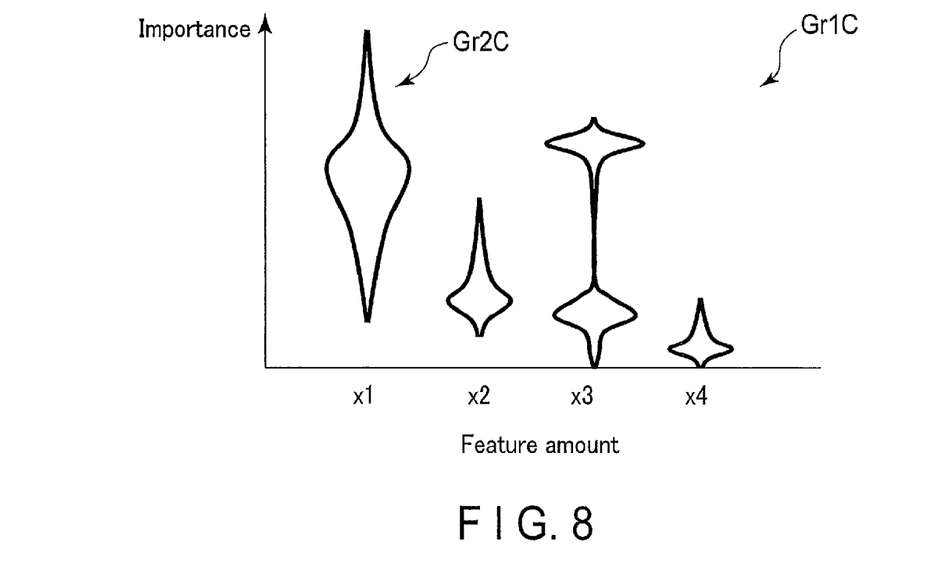
FIG. 8 shows another display example (without grouping) of the violin plot.

In the above embodiment, the distribution calculator 13 classifies N input data samples #1 to #N into a plurality of groups using a grouping threshold. However, the present embodiment is not limited to this. The distribution calculator 13 need not necessarily classify the input data samples #1 to #N into a plurality of groups. In this case, the distribution calculator 13 calculates a distribution of importances $c^j$ of each of the J feature amounts $x^j$ across all of N input data samples #1 to #N. Then, the display controller 14 generates a graph showing distributions, and causes the graph to be displayed. Also in this case, the distribution may be any of a probability density function, an average, a standard deviation, a quantile, and the like. For example, when the distribution is a probability density function, a violin plot is generated as the graph.

FIG. 8 shows another display example of the violin plot. The violin plot in FIG. 8 shows, as an example, the case of no grouping. As shown in FIG. 8, the violin plot includes a first graph Gr1C in which the vertical axis represents importances $c^j$ and the horizontal axis represents J feature amounts $x^j$. The violin plot also includes a second graph Gr2C for each feature amount $x^j$, in which the vertical axis represents importances $c^j$ and the horizontal axis represents probability densities of the importance $c^j$. Since grouping is not performed, the second graph Gr2C symmetrically shows a single probability density function. The display example of FIG. 8 also enables observation of a distribution of importances of each feature amount $x^j$ across all of N input data samples #1 to #N.

Figure 9:
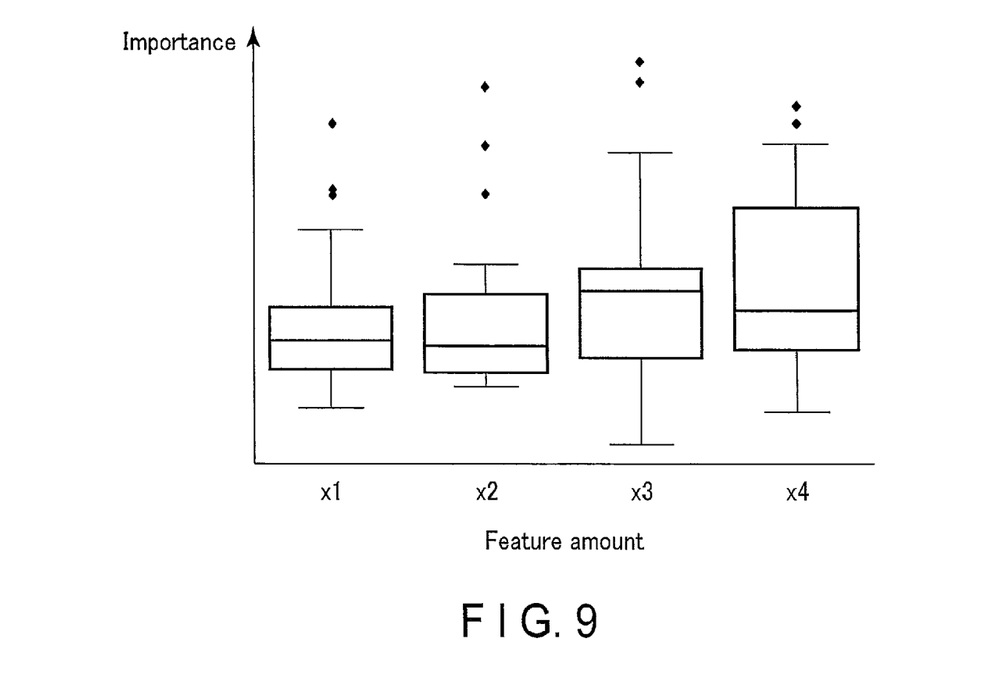
FIG. 9 shows a display example (without grouping) of a box plot.
Figure 10:
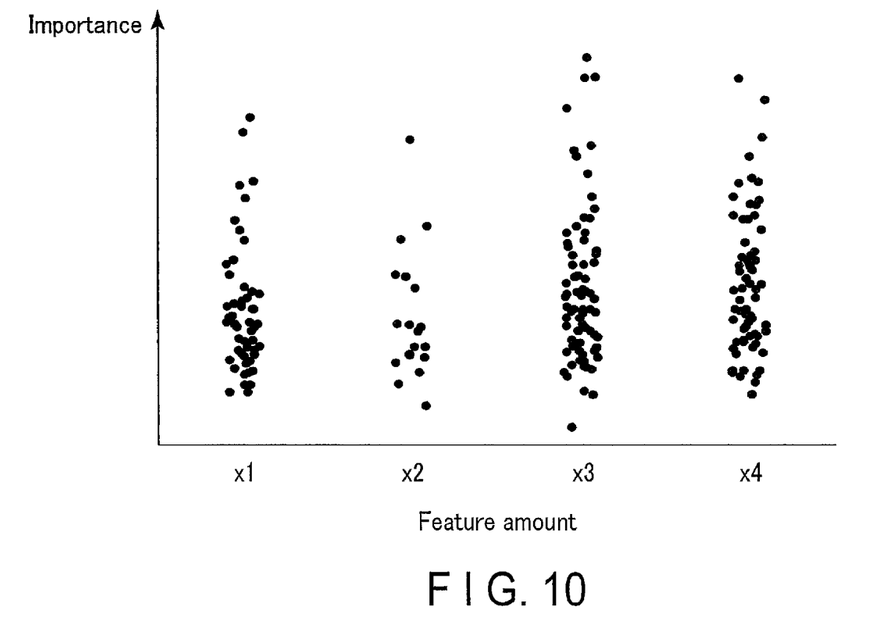
FIG. 10 shows a display example (without grouping) of a jitter plot.
Figure 11:
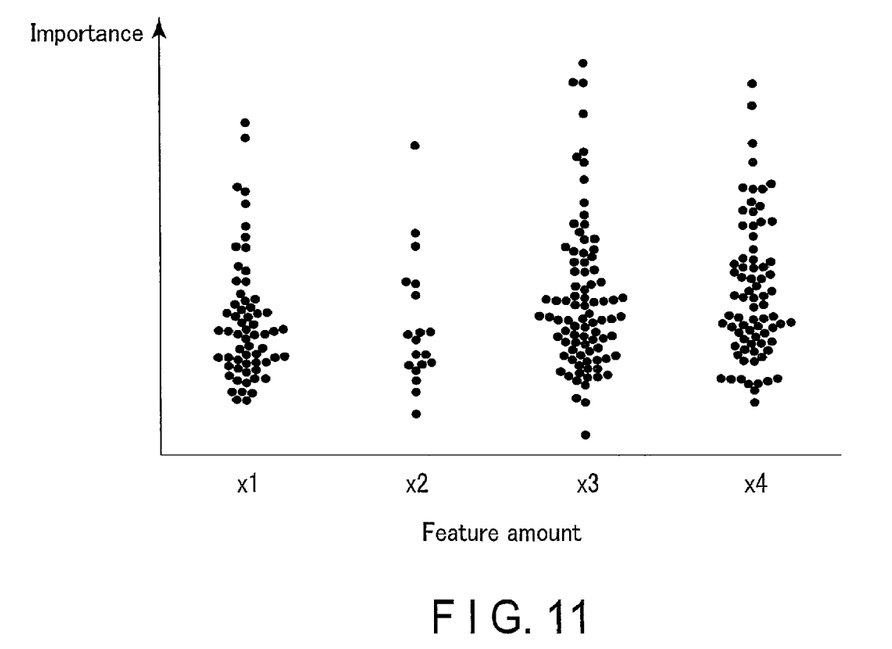
FIG. 11 shows a display example (without grouping) of a swarm plot.

The graph is not limited to the violin plot, and may be a box plot, a jitter plot, or a swarm plot. FIG. 9 shows a display example of the box plot, FIG. 10 shows a display example of the jitter plot, and FIG. 11 shows a display example of the swarm plot. Like the violin plot in FIG. 8, FIGS. 9, 10, and 11 each show the case of no grouping as an example. As shown in FIGS. 9, 10, and 11, the box plot, the jitter plot, and the swarm plot each include J graphs corresponding to J feature amounts $x^j$, in which the vertical axis represents importances $c^j$ and the horizontal axis represents J feature amounts $x^j$.

In the box plot shown in FIG. 9, a chart showing the density of importances $c^j$ by the size of a box is generated as a graph corresponding to each feature amount $x^j$. In the jitter plot shown in FIG. 10, a scatter plot in which plots of importances $c^j$ are scattered to the right and left is generated as a graph corresponding to each feature amount $x^j$. In the swarm plot shown in FIG. 11, a scatter plot in which plots of importances $c^j$ are scattered to the right and left while avoiding overlap is generated as a graph corresponding to each feature amount $x^j$. These graphs also enable observation of various distributions of importances. The box plot, jitter plot, and swarm plot may be used for a graph showing a distribution of importances $c^j$ for two or more groups.

The trained model is described as a neural network for multi-class classification and regression in the above-described embodiment; however, the trained model according to the present embodiment is not limited to this as long as it can define importances of each feature amount. For example, the trained model according to the present embodiment may be a decision tree ensemble type machine learning model, such as random forests, or a gradient boosting decision tree (GBDT), or may be any black box. In this case, tabular data in which numerical values are arranged in a tabular form may be input as input data.

As described above, the importance analysis apparatus 100 includes an importance calculator 12 and a distribution calculator 13. Based on a trained model and a plurality of input data samples, the importance calculator 12 calculates an importance of each of a plurality of feature amounts of each of the input data samples. The distribution calculator 13 calculates a distribution of importances of each of a plurality of feature amounts across the input data samples.

The above-described configuration enables calculation of importances across all input data samples, and thus can evaluate the importances of each feature amount across all input data samples. The configuration also reduces the possibility of overlooking the case where there are feature amounts of high importances only in some input data samples out of all input data samples, the case where a distribution of importances is multimodal, or the like.

The function of each unit according to the present embodiment, and the program for causing a computer to implement the function may be stored in a non-transitory computer readable medium.

Accordingly, the present embodiment can improve accuracy of analysis of an importance of a feature amount in machine learning.

While certain embodiments have been described, these embodiments have been presented by way of example only, and are not intended to limit the scope of the inventions. Indeed, the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

What is claimed is:

1. An importance analysis apparatus comprising:
processing circuitry configured to:
calculate estimated output values respectively by applying a plurality of input data samples to a trained model stored in a memory, wherein the trained model is a yield estimation model for semiconductor manufacturing chips, and the estimated output values represent a defectiveness and/or non-defectiveness determination result for semiconductor chips captured in the input data samples;
receive input data including optical image data acquired through optical imaging of a plurality of semiconductor chips, wherein the optical image data is provided as input to the trained model to determine semiconductor chip quality:
perform forward propagation processing on each of the input data samples through the trained model to generate a plurality of feature amounts, wherein each of the input data samples includes J feature amounts corresponding to J dimensions, and the feature amounts include feature maps or feature vectors derived from convolution layers of the trained model, or numerical/statistical representations derived from the input data samples;
calculate, based on the trained model and the plurality of input data samples, an importance of each of a plurality of feature amounts for each of the input data samples in relation to a yield estimation process;
calculate a distribution of the importances of each of the feature amounts across the input data samples by dividing the input data samples into a plurality of groups in accordance with the estimated output values, wherein the estimated output values include at least one of a number of defective and/or non-defective semiconductor chips, a defectiveness and/or non-defectiveness probability, a label indicating a defect type of a defective semiconductor chip, or a determination result for each semiconductor chip or pixel of the optical image data;

generate a structured dataset storing distribution values of the importance distributions for each of the groups;

apply a computer-implemented adaptive visual effect, including at least a flashing effect, wherein the flashing effect is triggered in real-time upon detecting a difference in distribution values between the groups exceeding a dynamically determined threshold based on system parameters; and cause a graphical user interface (GUI) of a computing device to render a dynamically updated graph with the applied visual effect, thereby enhancing interpretability of feature importance variations of the importances of each of the feature amounts across the groups, facilitating defect analysis in semiconductor chip manufacturing.

2. The apparatus according to claim 1, wherein the processing circuitry is further configured to apply a threshold to the estimated output values to divide the input data samples into the groups.

3. The apparatus according to claim 2, wherein the threshold comprises one threshold.

4. The apparatus according to claim 2, wherein the threshold comprises two or more thresholds.

5. The apparatus according to claim 1, wherein the graph is a first graph defined by the importances and the feature amounts, the distribution of each of the feature amounts is a second graph generated for each of the groups and defined by the importances and distribution values indicating frequencies of occurrence of the importances, and the second graphs of the respective feature amounts are aligned in such a manner that the directions of axes of the importances match that of the first graph.

6. The apparatus according to claim 1, wherein the processing circuitry is further configured to align the distributions of the respective feature amounts in descending order of difference in the distribution between the groups.

7. The apparatus according to claim 1, wherein the processing circuitry is further configured to enhance a distribution of the distributions of the respective feature amounts, in which the difference in distribution values between the groups is larger than the threshold.

8. The apparatus according to claim 1, wherein the processing circuitry is further configured to cause the distribution to be displayed in a different visual aspect for each of the groups.

9. The apparatus according to claim 1, wherein the graph is a violin plot, a box plot, a jitter plot, a swarm plot, or a ridgeline plot.

10. The apparatus according to claim 1, wherein the processing circuitry is further configured to calculate, as the distribution, a probability density function of the importances of each of the feature amounts across the input data samples.

11. The apparatus according to claim 1, wherein the processing circuitry is further configured to calculate the feature amounts by applying each of the input data samples to the trained model.

12. An importance analysis method, implemented by processing circuitry, the importance analysis method comprising:

calculating estimated output values respectively by applying a plurality of input data samples to a trained model stored in a memory, wherein the trained model is a yield estimation model for semiconductor manufacturing chips, and the estimated output values represent a defectiveness and/or non-defectiveness determination result for semiconductor chips captured in the input data samples;

receiving input data including optical image data acquired through optical imaging of a plurality of semiconductor chips, wherein the optical image data is provided as input to the trained model to determine semiconductor chip quality;

performing forward propagation processing on each of the input data samples through the trained model to generate a plurality of feature amounts, wherein each of the input data samples includes J feature amounts corresponding to J dimensions, and the feature amounts include feature maps or feature vectors derived from convolution layers of the trained model, or numerical/statistical representations derived from the input data samples;

calculating, based on the trained model and the plurality of input data samples, an importance of each of a plurality of feature amounts for each of the input data samples in relation to a yield estimation process;

calculating a distribution of the importances of each of the feature amounts across the input data samples by dividing the input data samples into a plurality of groups in accordance with the estimated output values, wherein the estimated output values include at least one of a number of defective and/or non-defective semiconductor chips, a defectiveness and/or non-defectiveness probability, a label indicating a defect type of a defective semiconductor chip, or a determination result for each semiconductor chip or pixel of the optical image data;

generating a structured dataset storing distribution values of the importance distributions for each of the groups;

applying a computer-implemented adaptive visual effect, including at least a flashing effect, wherein the flashing effect is triggered in real-time upon detecting a difference in distribution values between the groups exceeding a dynamically determined threshold based on system parameters; and causing a graphical user interface (GUI) of a computing device to render a dynamically updated graph with the applied visual effect, thereby enhancing interpretability of feature importance variations of the importances of each of the feature amounts across the groups, facilitating defect analysis in semiconductor chip manufacturing.

13. A non-transitory computer readable medium including computer executable instructions, wherein the instructions, when executed by a processor, cause the processor to:

calculate estimated output values respectively by applying a plurality of input data samples to a trained model stored in a memory, wherein the trained model is a yield estimation model for semiconductor manufacturing chips, and the estimated output values represent a defectiveness and/or non-defectiveness determination result for semiconductor chips captured in the input data samples;

receive input data including optical image data acquired through optical imaging of a plurality of semiconductor chips, wherein the optical image data is provided as input to the trained model to determine semiconductor chip quality;

perform forward propagation processing on each of the input data samples through the trained model to generate a plurality of feature amounts, wherein each of the input data samples includes J feature amounts corresponding to J dimensions, and the feature amounts include feature maps or feature vectors derived from convolution layers of the trained model, or numerical/statistical representations derived from the input data samples;

calculate, based on the trained model and the plurality of input data samples, an importance of each of a plurality of feature amounts for each of the input data samples in relation to a yield estimation process;

calculate a distribution of the importances of each of the feature amounts across the input data samples by dividing the input data samples into a plurality of groups in accordance with the estimated output values, wherein the estimated output values include at least one of a number of defective and/or non-defective semiconductor chips, a defectiveness and/or non-defectiveness probability, a label indicating a defect type of a defective semiconductor chip, or a determination result for each semiconductor chip or pixel of the optical image data;

generate a structured dataset storing distribution values of the importance distributions for each of the groups;

apply a computer-implemented adaptive visual effect, including at least a flashing effect, wherein the flashing effect is triggered in real-time upon detecting a difference in distribution values between the groups exceeding a dynamically determined threshold based on system parameters; and cause a graphical user interface (GUI) of a computing device to render a dynamically updated graph with the applied visual effect, thereby enhancing interpretability of feature importance variations of the importances of each of the feature amounts across the groups, facilitating defect analysis in semiconductor chip manufacturing.

* * * * *